US009036141B2

United States Patent
Obuchi et al.

(10) Patent No.: US 9,036,141 B2
(45) Date of Patent: May 19, 2015

(54) SURFACE INSPECTION APPARATUS AND SURFACE INSPECTION METHOD

(75) Inventors: Terumi Obuchi, Hitachinaka (JP); Hiroshi Kikuchi, Hitachi (JP); Yuji Inoue, Hitachinaka (JP); Nobuhiro Obara, Hitachinaka (JP); Kazuo Takahashi, Ninomiya (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 352 days.

(21) Appl. No.: 13/526,989

(22) Filed: Jun. 19, 2012

(65) Prior Publication Data

US 2012/0327403 A1     Dec. 27, 2012

(30) Foreign Application Priority Data

Jun. 27, 2011    (JP) .................................. 2011-141952

(51) Int. Cl.
G01N 21/00 (2006.01)
G01N 21/88 (2006.01)
G01N 21/95 (2006.01)

(52) U.S. Cl.
CPC ........ *G01N 21/8851* (2013.01); *G01N 21/9501* (2013.01)

(58) Field of Classification Search
CPC ... G01N 21/47; G01N 21/94; G01N 21/9501; G01N 21/956; G01N 21/8851; G01N 21/21; G01N 21/4738; G01N 21/55; G01N 21/8806; G01N 2021/8928; G01N 2021/4707; G01N 2021/4792; G01N 2021/8864; G01N 2021/8896

USPC ............................................. 356/237.1–237.5
See application file for complete search history.

(56) References Cited

U.S. PATENT DOCUMENTS

| 2005/0249395 | A1* | 11/2005 | Miller | 382/145 |
| 2006/0143425 | A1* | 6/2006 | Igarashi et al. | 711/173 |
| 2008/0239292 | A1* | 10/2008 | Kawaki et al. | 356/73 |
| 2011/0063603 | A1* | 3/2011 | Nakano et al. | 356/51 |

FOREIGN PATENT DOCUMENTS

JP      2010-140961     6/2010

* cited by examiner

*Primary Examiner* — Tarifur Chowdhury
*Assistant Examiner* — Sunghee Y Gray
(74) *Attorney, Agent, or Firm* — Brundidge & Stanger, P.C.

(57) ABSTRACT

A surface inspection apparatus includes a blocking unit included in a subsequent processing unit that groups data items into having an arbitrary number of data items. The subsequent processing unit acquires a data item from each of the blocks. The blocking unit changes, in accordance with an instruction transmitted from a state monitoring unit, the number of data items to be blocked. A threshold processing unit acquires data items from the blocking unit that have values larger than a threshold, and transmits the data items to a memory. The state monitoring unit monitors an available capacity of the memory. When the state monitoring unit detects a reduction in the available capacity of the memory, it causes the blocking unit to increase the number of data items to be blocked into each of the blocks so that data does not overflow from the memory.

9 Claims, 7 Drawing Sheets

720

SURFACE INSPECTION APPARATUS AND SURFACE INSPECTION METHOD

BACKGROUND OF THE INVENTION

1. Field of the Invention

The present invention relates to a surface inspection apparatus and a surface inspection method which detect minute foreign particles or defects on the surface of a specimen.

2. Description of the Related Art

In recent years, a surface inspection apparatus has been demanded for higher sensitivity and a higher throughput, and the amount of data to be processed is correspondingly increasing. Meanwhile, the surface inspection apparatus has been required for downsizing in view of the device volume and cost of the surface inspection apparatus.

JP-2010-140961-A discloses a technique for improving image processing in an appearance inspection apparatus for inspecting the state of a surface of a wafer.

JP-2010-140961-A involves monitoring the number, types and the like of processor elements that process and store information on the detected surface. Thus image division/distribution control is performed based on the states of connection of the processor elements so that fault tolerance for the processor elements is improved.

If any of the processor elements fails, an image distribution controller redistributes information to be stored by the faulty processor element and causes a normal processor element connected to the appearance inspection apparatus to store the information, and the appearance inspection apparatus continuously performs an inspection at a reset speed.

SUMMARY OF THE INVENTION

As described above, the technique disclosed in JP-2010-140961-A is such that detected continuous image data is divided into images that are units to be processed, and the divided images are distributed to predetermined normal processor elements. In order to cope with a change in the number of processor elements caused by failure of a processor element, the states of the processor elements are monitored and thereby the sizes of images to be distributed and the detection speed are reset in response to the states of the processor elements.

According to the technique disclosed in JP-2010-140961-A, however, if the number of normal processor elements connected to the apparatus decreases due to failure of a processor element or the like, surface detection speed will also decrease.

The decrease in the detection speed is compensated for by increasing the number of processor elements or the number of boards to be processed. The ratio of the area of a signal processing unit to the area of the apparatus, however, is increased, and thereby the size and cost of the apparatus may increase.

For example, if a wafer has much stain on the surface thereof, the amount of data to be processed is large accordingly. To address this, it is necessary to arrange a high-performance signal processing device or perform a data amount reduction process that extracts only necessary data.

There is, however, a problem with the cost if the high-performance signal processing device is to be arranged. In contrast the data amount reduction process can be achieved by a comparatively low-performance signal processing device, and is advantageous in terms of the cost. The stain on the surface of the wafer, however, is uncertain to expect. Thus, it is not ensured that the data amount reduction process is achieved while the accuracy of detection is maintained.

Currently, when there is a wafer for which the amount of data that is to be stored exceeds the capacity of a memory, it will be not ensured that such a wafer can be accurately inspected using only the data stored in the memory. Consequently, necessary conditions are reset by trial and error and the wafer is subjected to inspection again.

This is due to the fact that when data to be stored overflows from the memory, during the inspection of the surface of the wafer the content of data stored in the memory is updated and data stored so far in the memory is lost.

An object of the present invention is to achieve a surface inspection apparatus and a surface inspection method which avoid overflow of data to be stored and enable inspection data of a whole surface of a wafer to be obtained without a reduction in an inspection speed and an increase in the ratio of the area of a signal processing unit to the area of the apparatus.

In order to accomplish the aforementioned object, the surface inspection apparatus performs the following operations and the surface inspection method is performed as follows.

A specimen that is placed on a sample stage is irradiated with light. Light that is scattered from the specimen is detected by a plurality of scattered light detectors. The scattered light detectors output detection signals. The detection signals output from the plurality of scattered light detectors are combined. A plurality of data items that indicate the combined detection signals are blocked into blocks that are each a single unit. A data item is selected from among each of the blocks and stored in a memory. The number of data items to be blocked into each of the blocks is changed by a state monitoring unit on the basis of an available capacity of the memory. The data items that are stored in the memory are processed, and whereby a defect on a surface of the specimen is classified.

The surface inspection apparatus and the surface inspection method avoid the overflow of the data to be stored and enable the inspection data of the whole surface of the wafer to be obtained without the reduction in the inspection speed and the increase in the ratio of the area of the signal processing unit to the area of the apparatus.

DESCRIPTION OF THE PREFERRED EMBODIMENTS

An embodiment of the present invention is described with reference to the accompanying drawings.

Embodiment

Figure 1:
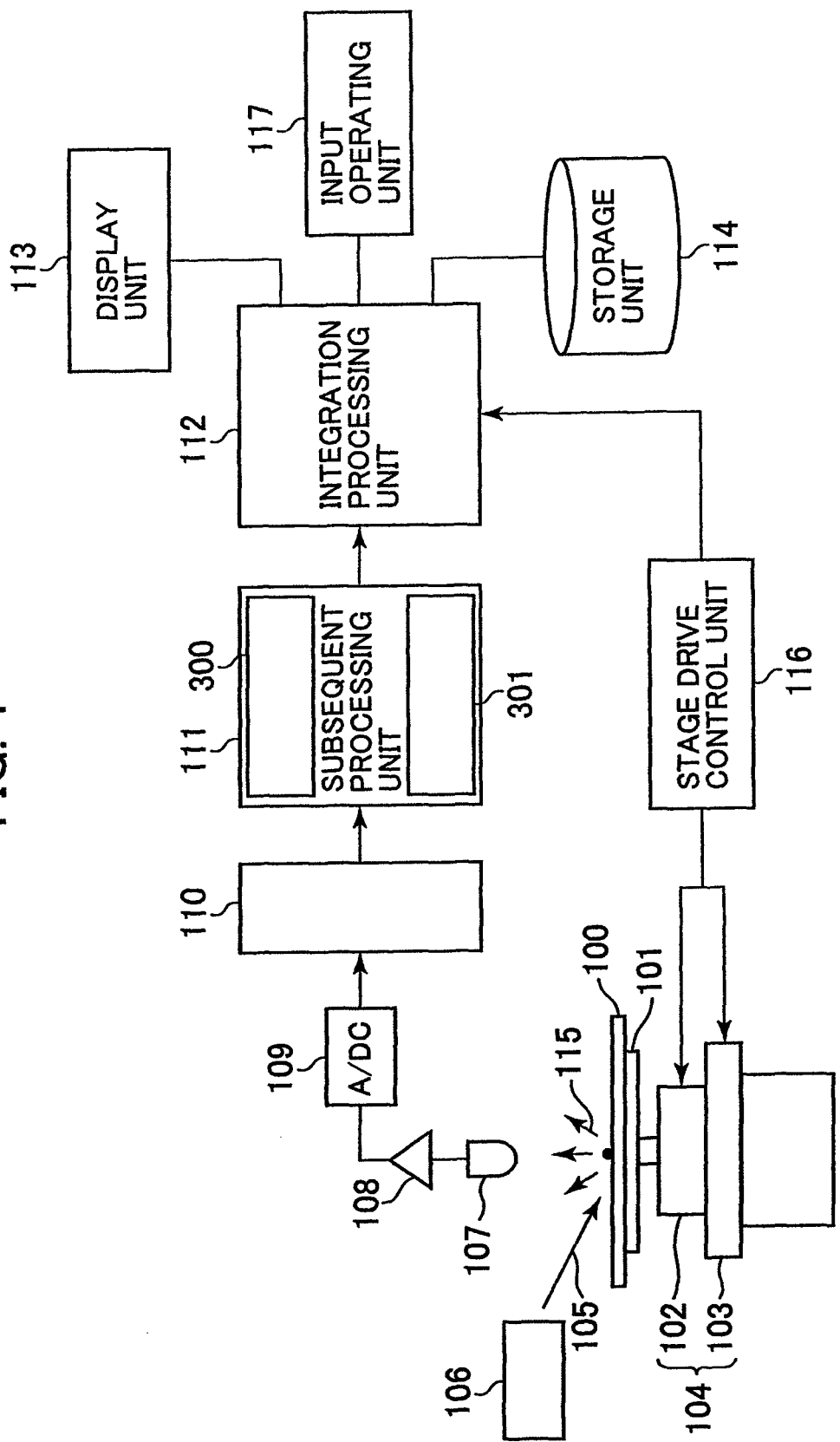
FIG. 1 is a diagram illustrating an outline configuration of a surface inspection apparatus according to an embodiment of the present invention.

FIG. 1 is a diagram illustrating an outline configuration of a surface inspection apparatus according to the embodiment of the present invention.

Referring to FIG. 1, the surface inspection apparatus according to the embodiment of the present invention includes a sample stage 101, a stage driving unit 104, an illumination unit 106, scattered light detectors 107, an amplifier 108, an A/D converter 109, a preprocessing unit 110, a subsequent processing unit 111, an integration processing unit 112, a display unit 113, a storage unit 114, a stage drive control unit 116 and an input operation unit 117.

A sample (for example, a wafer) 100 that is placed on the sample stage 101 is irradiated with light 105 by the illumination unit 106. Light 115 that is scattered from the wafer 100 (that is a specimen) is detected by the scattered light detectors 107 that output detection signals. The preprocessing unit 110 reduces noise of the detection signals output from the scattered light detectors 107, and then the subsequent processing unit 111 determines whether or not a defect exists on the wafer 100. The integration processing unit 112 combines the signals processed by the subsequent processing unit 112.

(1) Sample Stage 101

The sample stage 101 is described below.

The sample stage 101 holds the wafer 100 that is placed on the sample stage 101 and is the specimen. The sample stage 101 is rotationally driven by the stage driving unit 104. The stage driving unit 104 includes a rotary stage 102 and a slide stage 103. The rotary stage 102 rotates the sample stage 101. The slide stage 103 moves the sample stage 101 in a radial direction of the sample stage 101.

(2) Illumination Unit 106

Next, the illumination unit 106 is described.

The illumination unit 106 is arranged above the sample stage 101. The light 105 is emitted by the illumination unit 106 and formed in a spot-like shape so that the wafer 100 that is placed on the sample stage 101 is irradiated with the light 105. While the wafer 100 which is the sample is irradiated with the light 105, the sample stage 101 is moved in the radial direction by the slide stage 103 while being rotated by the rotary stage 102 so that the whole surface of the wafer 100 is relatively scanned with the light 105 in a spiral manner.

The stage drive control unit 116 controls driving mechanisms such as the rotary stage 102 and the slide stage 103. The stage drive control unit 116 can detect a coordinate position of inspection data on the wafer 100 on the basis of the driving position of the sample stage 101 controlled by the stage drive control unit 116.

(3) Scattered Light Detectors 107

Next, the scattered light detectors 107 are described.

The scattered light detectors 107 are connected to the amplifier 108 and the A/D converter 109. When the wafer 100 is irradiated with the light 105 emitted by the illumination unit 106, the light 105 hits a particle or a defect, the light 115 is scattered from the surface of the wafer 100 and then detected by the scattered light detectors 107.

The detection signals that are output from the scattered light detectors 107 are amplified by the amplifier 108. Then, the A/D converter 109 converts the amplified signals into digital signals. The number of scattered light detectors 107 is not limited. It is sufficient if the number of scattered light detectors 107 is two or more.

(4) Preprocessing Unit 110

Next, the preprocessing unit 110 is described.

The preprocessing unit 110 performs digital processing on the digitized signals converted by the A/D converter 109 and thereby reduces noise.

(5) Subsequent Processing Unit 111

Next, the subsequent processing unit 111 is described.

The subsequent processing unit 111 includes a blocking unit 300 and a threshold processing unit 301. The subsequent processing unit 111 performs a process of reducing the amount of data output from the preprocessing unit 110.

(6) Integration Processing Unit 112

The integration processing unit 112 is described below.

The integration processing unit 112 combines the signals (data) detected by the plurality of scattered light detectors 107 and processed and classifies a defect.

(7) Display Unit 113

The display unit 113 is described below.

The display unit 113 displays a map (called "defect map" for convenience) that represents data of a defect existing on the wafer 100. In addition, the display unit 113 displays combined data generated on the basis of the signals that have been processed by the integration processing unit 112 in accordance with conditions specified by the input operating unit 117, for example. Furthermore, the display unit 113 displays a map (called "block map" for convenience) that represents a change in the number of data items blocked in each of blocks of the wafer 100. The display unit 113 also displays a map (called "defect density map" for convenience) that represents the density of defects. The display unit 113 also displays conditions (for example, a recipe) for detection and the like.

The display unit 113 uses a display switch and can thereby individually display the defect map, the block map and the defect density map on the same screen. In addition, the display unit 113 uses the display switch and can thereby display the defect map, the block map and the defect density map on the screen so that the defect map, the block map and the defect density map overlap each other. Furthermore, the display unit 113 uses the display switch and can thereby singularly display any of the defect map, the block map and the defect density on the screen.

(8) Storage Unit 114

The storage unit 114 is described below.

The storage unit 114 stores programs and constant numbers, while the programs and the constant numbers are necessary for various types of control and calculations. In addition, the storage unit 114 stores inspection results (defect inspection data, combined data, the number of data items to be blocked into each of blocks, and threshold data), the conditions set by the input operating unit 117 and the like. Among the inspection results, the threshold data and the number of data items to be blocked into each of the blocks are stored, changed, modified and set by the integration processing unit 112.

Next, details of a surface inspection method according to the embodiment of the present invention are described with reference to FIG. 2.

Figure 2:
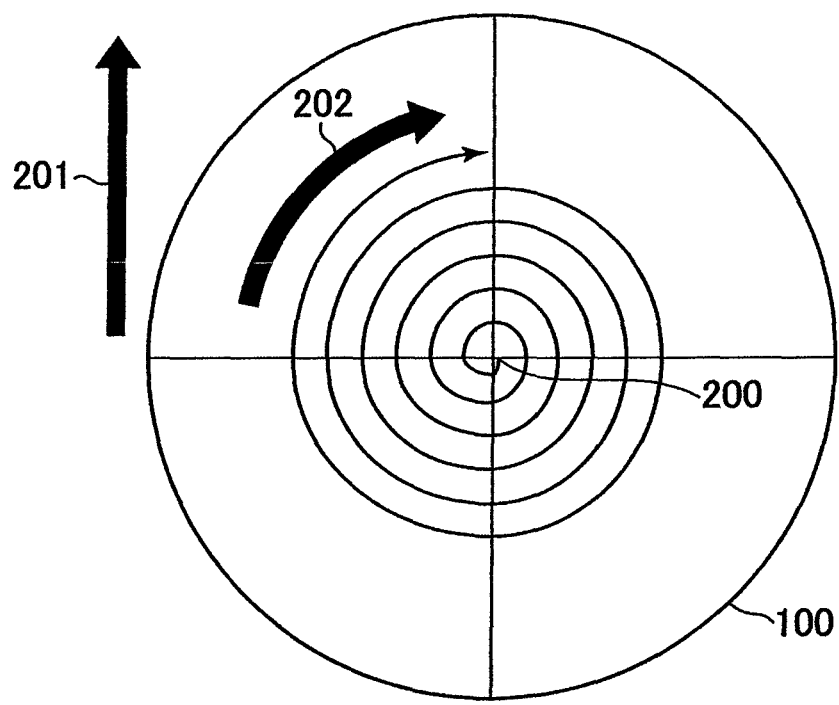
FIG. 2 is a diagram explaining a surface inspection method.

Referring to FIG. 2, when an inspection operation starts, the wafer 100 is rotated in a direction 202 (direction θ) around a point (the center of the wafer 100) 200 that is located on the wafer 100 and at which data starts to be acquired. While the wafer 100 is moved in a direction 201 (radial direction R), data is acquired from the surface of the wafer 100. When the wafer 100 is moved over a distance corresponding to the radius of the wafer 100, inspection data of the whole surface of the wafer 100 can be acquired. When the inspection data of the whole surface of the wafer 100 is acquired, the inspection operation is completed.

Next, details of the subsequent processing unit 111 are described with reference to FIG. 3.

Figure 3:
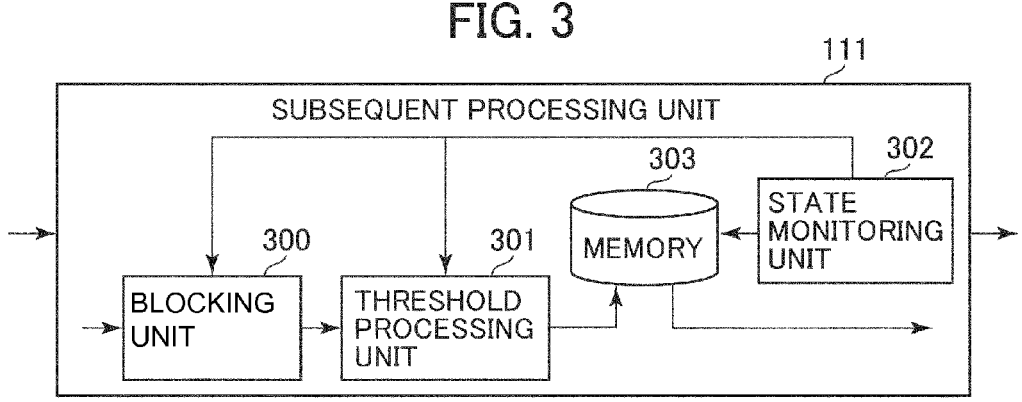
FIG. 3 is a diagram illustrating an internal configuration of a subsequent processing unit.

FIG. 3 is a diagram illustrating an internal configuration of the subsequent processing unit 111. Referring to FIG. 3, the blocking unit 300 groups an arbitrary number of the data signals subjected to the digital processing by the preprocessing unit 110 into each of blocks and extracts a single data item from each of the blocks. The blocking unit 300 changes the number of data items to be blocked into each of the blocks in accordance with an instruction transmitted from a state monitoring unit 302.

The threshold processing unit 301 determines whether or not a defect exists. The threshold processing unit 301 acquires only data items that are among data items input to the threshold processing unit 301 from the blocking unit 300 and larger than a threshold (for example, a threshold calculated on the basis of the acquired inspection data of the wafer 100) set in advance. The threshold processing unit 301 transmits the acquired data items to a memory 303. The threshold processing unit 301 can change the threshold in accordance with an instruction transmitted from the state monitoring unit 302. In addition, the threshold can be arbitrarily set from the input operating unit 117.

The state monitoring unit 302 monitors an available capacity of the memory 303 and instructs the blocking unit 300 to increase or reduce the number of data items to be blocked into each of the blocks. In addition, the state monitoring unit 302 can instruct the threshold processing unit 301 to change the threshold. Furthermore, the blocking unit 300 and the threshold processing unit 301 may be replaced with each other.

An operation that is performed by the blocking unit 300 to increase the number of data items to be blocked into each of the blocks is described below.

When the amount of data stored in the memory 303 increases and the state monitoring unit 302 detects a reduction in the available capacity of the memory 303, the state monitoring unit 302 instructs the blocking unit 300 to increase the number of data items to be blocked into each of the blocks. The blocking unit 300 increases the number of data items to be blocked into each of the blocks in accordance with the instruction transmitted from the state monitoring unit 302.

For example, when the available capacity of the memory 303 is reduced to 30% of the whole capacity of the memory 303, the state monitoring unit 302 causes the blocking unit 300 to increase the number of data items to be blocked into each of the blocks. After that, when the available capacity of the memory 303 is further reduced, the state monitoring unit 302 causes the blocking unit 300 to increase the number of data items to be blocked into each of blocks so that a data item does not overflow from the memory 303.

As another method for determining whether or not the number of data items to be blocked into each of the blocks is increased, the state monitoring unit 302 may perform the following operation. That is, the state monitoring unit 302 monitors an increased amount of data stored in the memory 303 on an hourly basis. When the increased amount of the data stored in the memory 303 reaches a certain value, the state monitoring unit 302 causes the blocking unit 300 to increase the number of data items to be blocked into each of the blocks. After the state monitoring unit 302 causes the blocking unit 300 to increase the number of data items to be blocked into each of the blocks, the state monitoring unit 302 monitors an increased amount of data stored in the memory 303 on an hourly bases. When the increased amount of the data stored in the memory 303 reaches the certain value, the state monitoring unit 302 causes the blocking unit 300 to increase the number of data items to be blocked into each of blocks.

The state monitoring unit 302 monitors the state of the memory 303. The state monitoring unit 302 instructs the blocking unit 300 to increase, reduce or maintain the number of data items to be blocked into each of the blocks. Details of instructions that are transmitted from the state monitoring unit 302 to increase and reduce the number of data items to be blocked into each of the blocks can be stored in the memory 303 or the state monitoring unit 302.

An example of a process that is performed in the case in which the blocking unit 300 and the threshold processing unit 301 are replaced with each other in the subsequent processing unit 111 illustrated in FIG. 3 is described below.

The threshold processing unit 301 acquires only data items with higher values than the threshold among the data items input to the subsequent processing unit 111 from the preprocessing unit 110. The threshold processing unit 301 outputs the acquired data items to the blocking unit 300. The blocking unit 300 groups the data items received from the threshold processing unit 301 into blocks and acquires data items extracted using another threshold as a reference. Then, the blocking unit 300 transmits the acquired data items to the memory 303.

The blocking unit 300 extracts, from each of the blocks, a single data item whose value is larger than the aforementioned other threshold. A plurality of inspection data items with larger values than the other threshold may exist in any of the blocks. Even in this case, the blocking unit 300 extracts a single data item from each of the blocks. The number of inspection data items with larger values than the other threshold can be displayed as the defect density map that represents a defect density (the number of defects) in each of the blocks.

Basic blocking operation that is performed by the blocking unit 300 (called "basic blocking unit" for convenience shake) is described with reference to FIG. 4.

The data blocking is to select a single representative point from among a plurality of detected data items 400. The detected data items 400 are the intensities of the light scattered and detected at each of angles θ.

Figure 4:
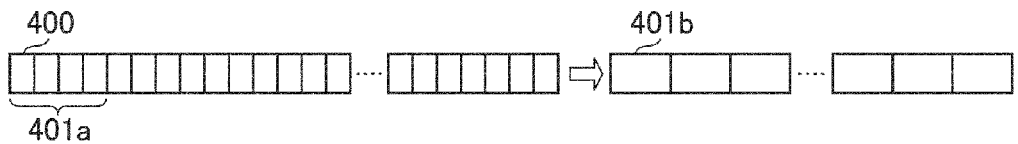
FIG. 4 is a diagram explaining an operation of blocking data items into blocks by means of a blocking unit.

FIG. 4 illustrates the case in which the detected data items 400 are blocked into blocks each including data items whose number is indicated by 401a, and a single detected data item 401b is extracted from each of the blocks that each includes data items whose number is indicated by 401a. A single data item is extracted from each of the blocks. The data item 401b, which is extracted from each of the blocks that each include data items whose number is indicated by 401a, has the largest value (or the maximum value) among data items 400 blocked in the block.

When the data items are blocked into the blocks, a plurality of data items are included in each of the blocks. When a plurality of data items is to be detected, there is a problem that only a single data item may be detected. This problem can be solved by setting a range to be blocked in each of the blocks to a value that is smaller than a resolution capability of an optical apparatus. Thus, a plurality of data items to be detected does not exist in each of the blocks. The data blocking can reduce the amount of data to be processed per time unit.

Next, details of the blocking unit 300 according to the embodiment of the present invention are described with reference to FIG. 5.

A method for blocking data is the same as the aforementioned basic blocking.

Figure 5:
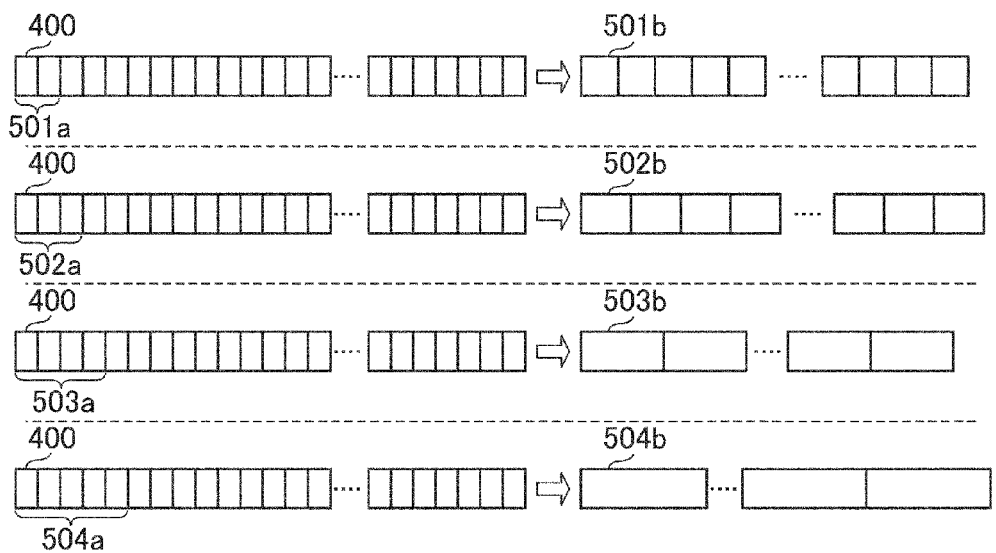
FIG. 5 is a diagram explaining the operation of blocking data items into blocks by means of the blocking unit.

FIG. 5 is a diagram illustrating cases in which the detected data items 400 are blocked into blocks (including data items whose numbers are indicated by 501a to 504a), and detected data items 501b to 504b are extracted from the blocked data items. FIG. 5 illustrates processing that is performed when the number of data items to be blocked into each of blocks varies depending on the state of the surface of the wafer 100. The detected data items 400 are blocked into blocks that include the different numbers 501a to 504a of data items.

An example of an operation that is performed when the number of data items to be blocked into each of blocks varies depending on the state of the surface of the wafer 100 is described below.

Referring to FIG. 5, when the number of data items to be blocked into each of blocks is two (501a), two detected data items are treated as a single block, and a data item that is among the two detected data items and has a larger value than the other data item is treated as a detected data item 501b.

When the number of data items to be blocked into each of blocks is three (502a), three detected data items are treated as a single block, and a data item that is among the three data items and has the largest value among the three data items is treated as a detected data item 502b. The same applies to the cases in which the numbers of data items to be blocked into each of blocks are four (503a) and five (504a).

Figure 6:
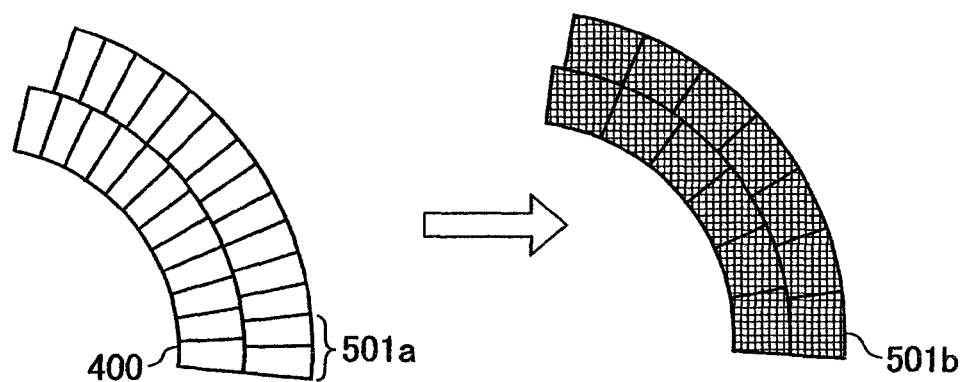
FIG. 6 is a diagram illustrating data items blocked in blocks.
Figure 6:
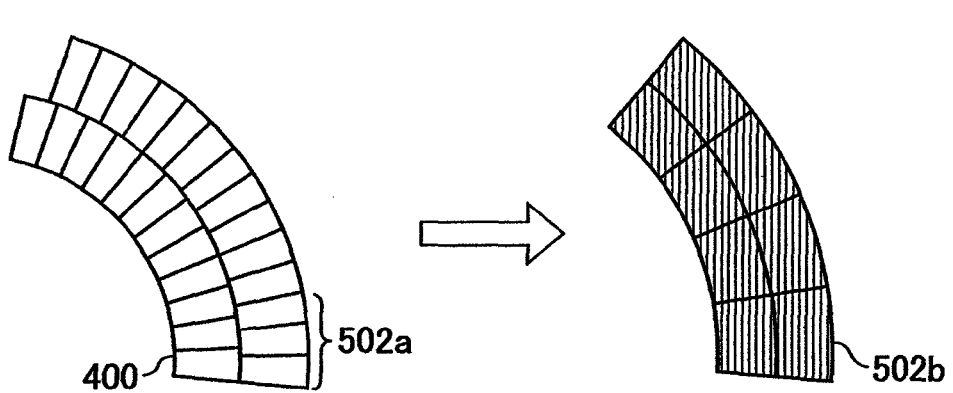

FIG. 6 is a diagram illustrating data items that are blocked into the blocks by the blocking unit 300 during the inspection of the wafer 100. FIG. 6 illustrates an example in which when the number of data items blocked in each of the blocks is two (501a), detected data items to be extracted are data items 501b. In addition, FIG. 6 illustrates an example in which when the number of data items blocked in each of the blocks is three (502a), detected data items to be extracted are data items 502b.

When a single wafer 100 is to be inspected, the number of data items to be blocked into each of blocks is not fixed and is variable and set on the basis of the available capacity of the memory 303.

For example, when the number of many particles that exist on the wafer 100 is large, the number of data items to be blocked into each of blocks is increased. When the number of particles that exist on the wafer 100 is small, the number of data items to be blocked into each of blocks is reduced.

Figure 7:
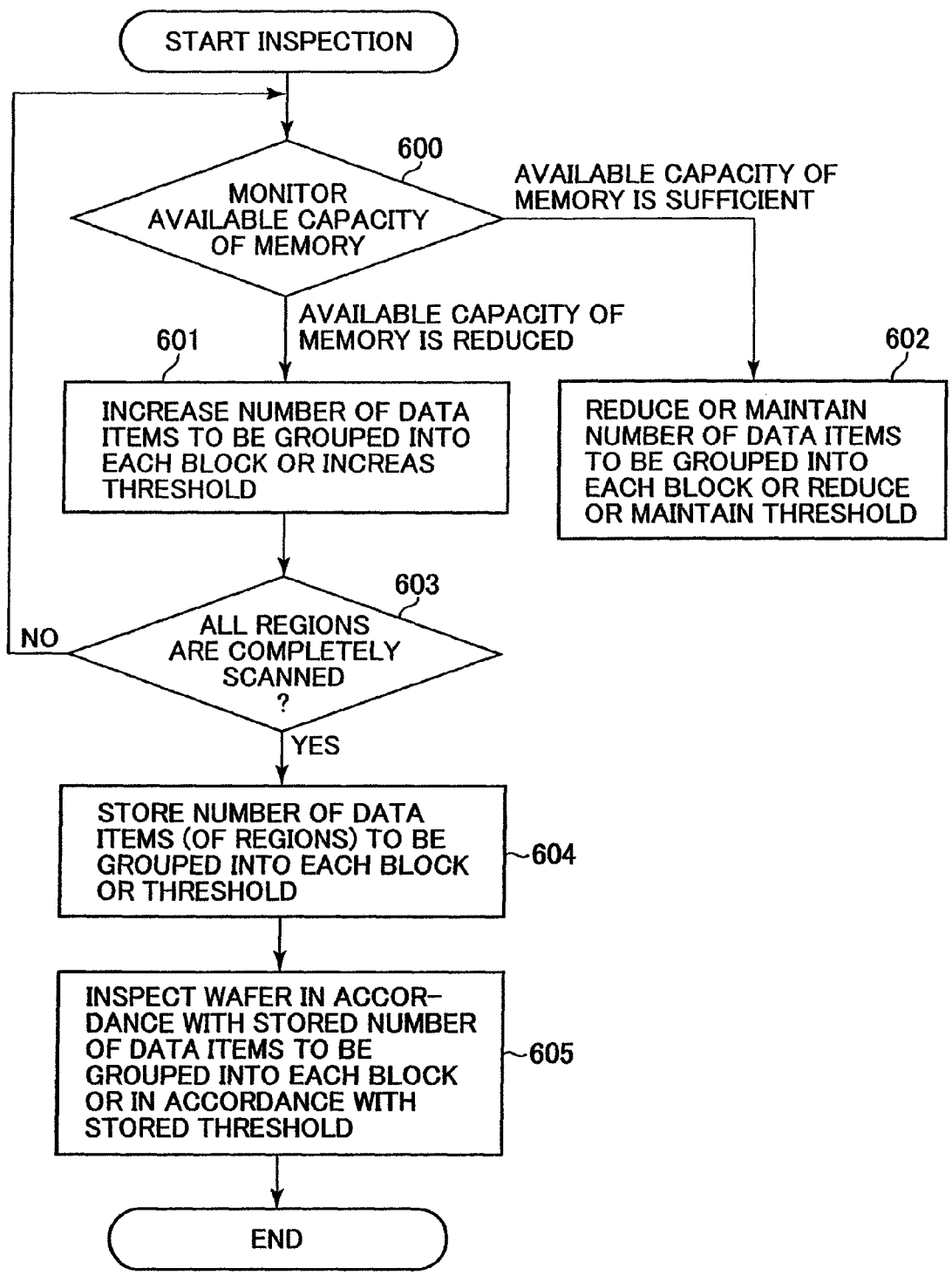
FIG. 7 is a flowchart of operations according to the embodiment of the present invention.

FIG. 7 is a flowchart of operations according to the embodiment of the present invention.

Referring to FIG. 7, when the surface inspection apparatus starts inspecting the wafer 100, the state monitoring unit 302 monitors the available capacity of the memory 303 and determines whether or not the available capacity of the memory 303 is sufficient (for example, is equal to or larger than 30% of the whole capacity of the memory 303) in step 600.

When the available capacity of the memory 303 is reduced due to an increase in the amount of data stored in the memory 303, data may easily overflow from the memory 303. When the available capacity of the memory 303 is reduced and the state monitoring unit 302 determines that the available capacity of the memory 303 is insufficient, a process illustrated in FIG. 7 proceeds to step 601 in order to avoid overflow of data from the memory 303. The state monitoring unit 302 instructs the blocking unit 300 to increase the number of data items to be blocked into each of blocks (or instructs the threshold processing unit 301 to increase the threshold) in step 601.

When the available capacity of the memory 303 is sufficient in step 600, the state monitoring unit 302 instructs the blocking unit 300 to reduce or maintain the current number of data items to be blocked into each of the blocks (or instructs the blocking unit 300 to reduce or maintain the threshold) in step 602.

In step 603, the state monitoring unit 302 and the integration processing unit 112 determine whether or not all regions (to be inspected) of the wafer 100 have been scanned. When any of all the regions (to be inspected) of the wafer 100 is yet to be scanned in step 603, the process returns back to step 600.

When all the regions (to be inspected) of the wafer 100 have been scanned in step 603, the process proceeds to step 604. In step 604, the number of data items (of regions, of the wafer 100, scanned and determined) blocked in each of the blocks or the threshold are to be stored in the storage unit 114 through the integration processing unit 112.

In step 605, the inspection of the wafer 100 restarts so that the wafer 100 is inspected in accordance with the number (stored in the storage unit 114) of data items (of regions of the wafer 100) to be blocked into each of blocks or in accordance with the threshold stored in the storage unit 114. Then, data (inspection data) of the inspected wafer 100 is stored in the memory 303.

Specifically, in the embodiment of the present invention, the initial inspection is performed on the wafer 100, the number of data items (of regions of the wafer 100) to be blocked into each of the blocks or the threshold is set, and the main inspection is performed on the wafer 100 in accordance with the set number of data items (of regions of the wafer 100) to be blocked into each of blocks or in accordance with the set threshold.

A user such as an operator can terminate the inspection after the completion of the initial inspection without the main inspection. In this case, the user uses the input operating unit 117 to set information on the inspection in the integration processing unit 112.

Figure 8:
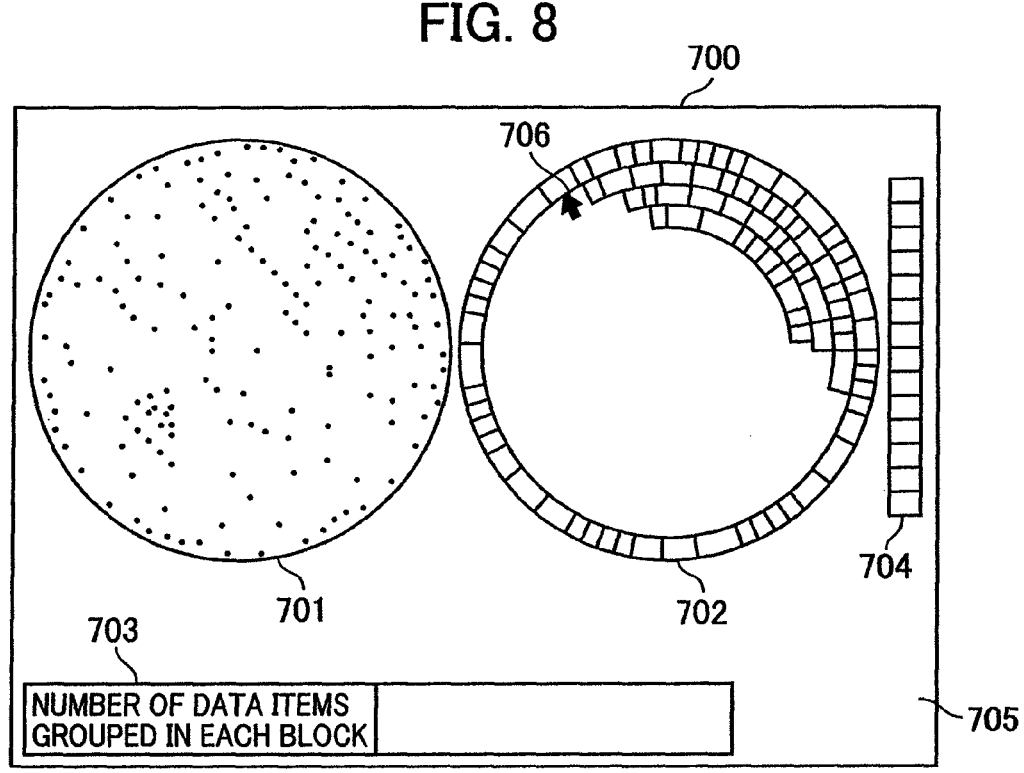
FIG. 8 is a diagram illustrating an example of an analysis screen displayed on a display unit according to the embodiment of the present invention.

FIG. 8 is a diagram illustrating an example of an analysis screen displayed on the display unit 113 according to the embodiment of the present invention.

As illustrated in FIG. 8, a defect map 701, a block map 702, a display region 703 and a color bar 704 are displayed in a display region 705 of an analysis screen 700. Data of defects on the wafer 100 is displayed in the defect map 701. A change in the number of data items blocked in each of blocks is displayed in the block map 702. The number of data items blocked in each of the blocks is displayed in the display region 703. The defect map 701 and the block map 702 are created by the integration processing unit 112.

The defect map 701 and the block map 702 may be replaced with each other as long as the defect map 701 and the block map 702 are displayed in the display region 705. The number of data items blocked in a block that is selected using a cursor 706 on the block map 702 through an operation of the input operating unit 117 or selected on the block map 702 by a user's touch of the display region 705 is displayed in the display region 703.

The blocks, which are displayed in the block map 702 and whose numbers of data items are different, may be distinguished by colors. In the color bar 704, the numbers of data items blocked in the blocks correspond to the colors.

Figure 9:
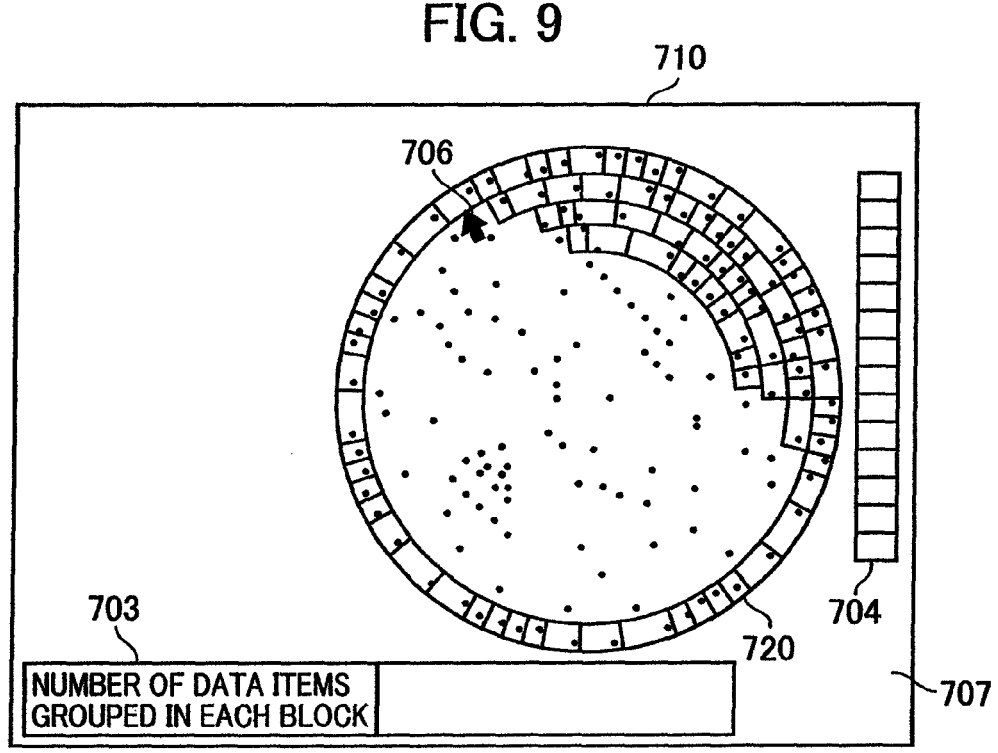
FIG. 9 is a diagram illustrating an example of a combination screen on which a defect map and a block map are displayed.

FIG. 9 is a diagram illustrating an example of a combination screen of which the defect map and the block map are displayed on the display unit 113.

A combination screen 710 illustrated in FIG. 9 is a screen to which the analysis screen 700 is changed by a display switch operation (for example, a user's touch of a display switch button displayed on the analysis screen 700 or an input operation performed by the input operating unit 117).

The display switch operation also enables the combination screen 710 to be changed to the analysis screen 700.

As illustrated in FIG. 9, an enlarged map 720, the display region 703 and the color bar 704 are displayed in a display region 707 of the combination screen 710.

Figure 10:
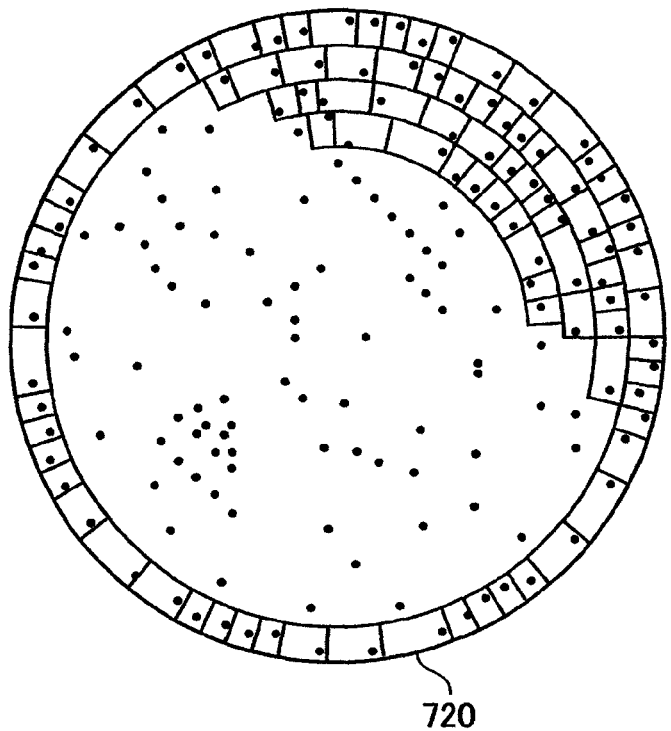
FIG. 10 is an enlarged view of a part of the combination screen displayed on the display unit.

FIG. 10 illustrates the enlarged map 702.

In the enlarged map 720, the defect map 701 and the block map 702 can be displayed so that the defect map 701 and the block map 702 overlap each other. In addition, the defect map 701 and the block map 702 can be individually displayed in the enlarged map 720. Blocking number of the blocked map 702 selected by the cursor 706 is displayed on the blocking number displaying region 703 by a user's touch to the blocking number display region 703, and the blocked map 702 is displayed on the enlarged map 720. The blocks, which are displayed in the block map 702 and whose numbers of data items are different, may be distinguished by colors. In the color bar 704, the numbers of data items blocked in the blocks correspond to the colors.

A distribution of defects and changes in the numbers of data items blocked in the blocks can be simultaneously confirmed by overlapping and displaying the defect map 701 and the block map 702 or by distinguishing, using colors, blocks whose numbers of data items are different and displaying the distinguished blocks. In addition, the blocks can be visually clear.

The defect density map (not illustrated) can be displayed on the display unit 113. The defect density map can be displayed separately from the defect map 701 and the block map 702 on the same screen. The defect density map can be displayed so that the defect density map overlaps the defect map 701 and the block map 702. Furthermore, only the defect density map can be displayed.

The threshold that is changed on the basis of an increase or reduction in the amount of the inspection data can be displayed on the display unit 113 as a threshold change map (not illustrated).

For example, when the number of data items to be blocked into each of blocks is fixed, and the inspection needs to be performed, the number (stored in the storage unit 114) of data items to be blocked into each of blocks may be manually set using the input operating unit 117 so that the number is increased or reduced. In addition, a data threshold (threshold to be used to select a data item from among each data block) that is stored in the storage unit 114 may be manually set so that the data threshold is increased or reduced.

The number of data items to be blocked into each of blocks and the threshold are changed on the basis of the available capacity of the memory and stored in the storage unit 114, while the numbers and the threshold can be manually changed and set.

As illustrated in FIG. 2, the start point 200 at which the data starts to be acquired in the surface defect inspection of the wafer 100 is the center of the surface of the wafer 100. The number of data items to be blocked into a block and the threshold tend to be increased as the inspection is progressed.

The number of data items to be blocked into a block or the threshold is increased toward an outer circumference of the wafer 100. The accuracy of the defect detection performed on the outer circumference of the wafer 100 may be lowered, compared with the accuracy of the defect detection performed on a region located near the center of the surface of the wafer 100.

When the main inspection is performed using the number (used for the initial inspection) of data items (of regions of the wafer 100) blocked in each of the blocks or the threshold (used for the initial inspection), it is considered that the accuracy of the defect detection in the initial inspection is rarely different from the accuracy of the defect detection in the main inspection.

It is, however, considered that the number of data items blocked in a block located near the outer circumference of the wafer 100 or a threshold for the block located near the outer circumference of the wafer 100 is used for the main inspection in consideration of results of the initial inspection.

In this case, the number (used for the main inspection) of data items blocked in a block located near the center of the surface of the wafer 100 is larger than the number (used for the initial inspection) of data items blocked in the block located near the center of the surface of the wafer 100. The accuracy of the defect detection performed in the main inspection on a region located near the center of the surface of the wafer 100 may be lower.

The accuracy of the defect detection can be improved by using defect inspection results of the initial inspection for a region located near the center of the surface of the wafer 100.

Figure 11:
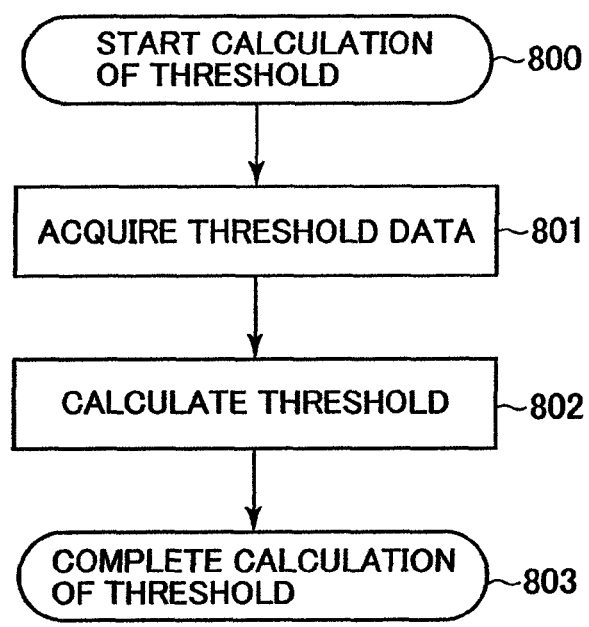
FIG. 11 is a flowchart of a sequence for calculating a threshold using inspection data.

FIG. 11 is a flowchart of an operation of calculating a threshold on the basis of threshold data. In order to calculate the threshold, the threshold data is acquired in sequence 801. The threshold (for example, the average of the threshold data or the maximum or minimum value of the threshold data) is calculated on the basis of the acquired threshold data in sequence 802. After sequence 802, the threshold can be automatically or manually set in the threshold processing unit 301. In sequence 803, the calculation of the threshold is terminated.

Since the inspection data of the whole surface of the wafer 100 is acquired, the inspection data can be used for setting of processing conditions.

According to the present invention, the available capacity of the memory 303 is monitored, and the amount of data to be stored is controlled on the basis of a reduction in the available capacity so that data does not overflow from the memory 303 before the acquisition of the defect inspection data. The surface inspection apparatus and the surface inspection method can be achieved, which avoid overflow of data from the memory and enable the inspection data of the whole surface of the wafer to be acquired without a reduction in the speed of the inspection and an increase in the ratio of the area of the signal processing unit to the area of the apparatus.

What is claimed is:

1. A surface inspection method for inspecting a surface of a specimen, comprising the steps of:
   irradiating the specimen placed on a sample stage with light;
   causing a plurality of scattered light detectors to detect light scattered from the specimen and output detection signals;
   combining the detection signals output from the plurality of scattered light detectors;
   blocking plural data into blocks of data, wherein each of the blocks represents intensities of the scattered light detected from the specimen at corresponding scattering angles, the detection signals combined by the step of combining the detection signals being signals of the plural data representing the intensities of the scattered light;

extracting one data selected from the plural data in each of the blocks, and storing the extracted data into a memory;

changing a number of the data blocked in at least one of the blocks by a state monitoring unit on the basis of an available capacity of the memory; and processing the extracted data stored in the memory to thereby classify defects on the surface of the specimen.

2. The surface inspection method according to claim 1, wherein a data whose value is larger than a set threshold is the data selected from the plurality data blocked in each of the blocks, and the threshold to be used to select a data is changed and set on the basis of the available capacity of the memory.

3. The surface inspection method according to claim 1, further comprising the steps of:

storing, as inspection data, data of the classified defect of the surface of the specimen; and displaying the inspection data on a display unit.

4. The surface inspection method according to claim 3, further comprising the steps of:

creating a defect map indicating a distribution of defects on the specimen and a block map indicating regions that are included in the specimen and correspond to the blocked plural data; and displaying at least one of the created block map and the created defect map on the display unit or displaying the created block map and the created defect map on the display unit so that the block map and the defect overlap each other.

5. The surface inspection method according to claim 4, wherein the defect map and the block map are displayed side by side on a single screen of the display unit.

6. The surface inspection method according to claim 3, further comprising the step of:

storing the number of data to be blocked into each of the blocks and the set threshold in a storage unit.

7. The surface inspection method according to claim 6, wherein the stored number of data to be blocked into each of the blocks and the stored threshold in the storage unit can be changed.

8. The surface inspection method according to claim 7, wherein the number of data to be blocked into each of the blocks and the threshold are changed on the basis of the available capacity of the memory and can be set to arbitrary values.

9. The surface inspection method according to claim 3, wherein the number of data to be blocked into each of the blocks is displayed on the display unit.

* * * * *